US008992655B2

(12) United States Patent
Posner et al.

(10) Patent No.: US 8,992,655 B2
(45) Date of Patent: Mar. 31, 2015

(54) METHODS FOR IMPROVING BUD BREAK

(76) Inventors: David Posner, Capitola, CA (US);
Stephen Pavich, Paradise Valley, AZ (US)

(*) Notice: Subject to any disclaimer, the term of this patent is extended or adjusted under 35 U.S.C. 154(b) by 456 days.

(21) Appl. No.: 13/178,366

(22) Filed: Jul. 7, 2011

(65) Prior Publication Data
US 2012/0060573 A1 Mar. 15, 2012

Related U.S. Application Data

(60) Provisional application No. 61/362,212, filed on Jul. 7, 2010.

(51) Int. Cl.
| | |
|---|---|
| *C05F 3/00* | (2006.01) |
| *C05F 11/00* | (2006.01) |
| *C01C 1/18* | (2006.01) |
| *C05G 1/00* | (2006.01) |
| *A01N 61/00* | (2006.01) |
| *C05G 3/00* | (2006.01) |
| *A01N 65/00* | (2009.01) |

(52) U.S. Cl.
CPC *C05G 1/00* (2013.01); *A01N 61/00* (2013.01); *C05F 11/00* (2013.01); *C05G 3/0064* (2013.01); *A01N 65/00* (2013.01)
USPC ........................................ 71/23; 71/22; 71/54

(58) Field of Classification Search
CPC ........ C05G 1/00; C05G 3/0064; C05F 11/00; A01N 61/00; A01N 65/00; A01N 65/03
USPC .................................................. 71/11–64.13
See application file for complete search history.

(56) References Cited

U.S. PATENT DOCUMENTS

| | | |
|---|---|---|
| 4,487,625 A | 12/1984 | Rieder |
| 5,451,240 A | 9/1995 | Trowbridge |
| 7,030,060 B1 * | 4/2006 | McDonald et al. ........ 504/116.1 |
| 2006/0179976 A1 | 8/2006 | Silva et al. |
| 2009/0099021 A1 | 4/2009 | Dean |

FOREIGN PATENT DOCUMENTS

WO 97/24926 A1 7/1997

OTHER PUBLICATIONS

Lecouteur, Landscape maintenance calendar for the mid-atlantic region, Jan. 1, 1994, XP055087744, Retrieved from the Internet: URL: https://www.mwcog.org/uploads/pub-documents/oV5eW1c20110901081110.pdf [retrieved on Nov. 12, 2013].

Hasselkus, Caring for deciduous shrubs, Jan. 1, 1999, pp. 1-4, XP055087753, Retrieved from the Internet: URL: http://learningstore.uwex.edu/pdf/A1771.POF [retrieved on Nov. 12, 2013].

Anonymous, Annual growth cycle of grapevines, From Wikipedia, the free encyclopedia, retrieved on Apr. 11, 2012, http://en.wikipedia.org/wiki/Annual_growth_cycle_of_grapevines.

Anonymous, Fertilizer, From Wikipedia, the free encyclopedia, retrieved on Apr. 10, 2012, http://en.wikipedia.org/wiki/Fertilizer.

Combs et al., Micronutrient Status of Manure, Department of Soil Science, University of Wisconsin—Madison, retrieved on Apr. 10, 2012, http://www.uwex.edu/ces/forage/wfc/proceedings2001/micronutrient_status_of_manure.htm.

Gutiérrez-Miceli et al., Formulation of a liquid fertilizer for sorghum (*Sorghum bicolor* (L.) Moench) using vermicompost leachate, Bioresource Technology, vol. 99, Issue 14, Sep. 2008, pp. 6174-6180, ISSN: 0960-8524.

Smith et al., Nutrient dynamics of a kiwifruit ecosystem, Scientia Horticulturae, vol. 37, Issues 1-2, Nov. 1988, pp. 87-109, ISSN: 0304-4238.

* cited by examiner

*Primary Examiner* — Jennifer A Smith
(74) *Attorney, Agent, or Firm* — McDonnell Boehnen Hulbert & Berghoff LLP

(57) ABSTRACT

Methods of inducing bud break of deciduous fruit vines, trees, or shrubs following dormancy by the application of bud breaker compositions that do not contain hydrogen cyanamide.

28 Claims, No Drawings

METHODS FOR IMPROVING BUD BREAK

This application claims priority to U.S. provisional application Ser. No. 61/362,212, filed Jul. 7, 2010, which is incorporated by reference herein in its entirety.

FIELD OF THE INVENTION

This invention relates to methods of inducing or improving bud break of deciduous plants, including fruit trees, grape and kiwifruit vines, shrubs, or bushes following dormancy by the application of a composition by either foliar application, drip (soil) application, or both, wherein the composition contains five or more of the components of the group consisting of nitrogen, phosphorus, potassium, calcium, magnesium, trace elements, acidifier, fulvic acid, and seaweed, and where the composition or compositions do not contain hydrogen cyanamide or any version or chemical equivalent of hydrogen cyanamide. The methods of this invention include, but are not limited to, inducing bud break of grapevines after forced dormancy in tropical or semi-tropical climates or after partial dormancy in temperate climates.

BACKGROUND OF THE INVENTION

Deciduous fruit trees, grape vines and kiwifruit vines, shrubs, or bushes normally require enough winter chilling hours to produce a crop of fruit. The amount of chilling required depends upon the kind of fruit and the cultivar. Problems can arise in tropical and semi-tropical climates when there is no chilling, or in desert climate zones where there is insufficient chilling. The result of these problems can be growth abnormalities such as delayed and uneven blossoming, poor leaf cover, and insufficient or inconsistent fruit-set and reduced fruit size can occur. At the end of a vegetation period, such plants cease growing after bearing fruit and form buds. This budding enables a meristem, which has undifferentiated leaf and blossom structures, to survive under the unfavorable environmental conditions of winter because buds, in the latent stage, are much more resistant to frost and low temperatures than active tips of vegetation. Without sufficient chilling, the buds can be devoid of a commercially acceptable yield of fruit.

This latent stage is referred to as dormancy, and its duration is species specific and depends upon environmental conditions, such as the degree-day chilling factor. Dormancy is generally initiated by exposing buds to sufficient degree days' chilling. This means that the dormancy can generally only be terminated if the buds have been exposed to degree days' chilling that are insufficient to continue dormancy, followed by an experience of elevated temperatures.

In grape and fruit growing areas, mild winters with dormancy that are either not strong enough, not long enough, or that are non-existent, can cause delayed or reduced bud break or development. The result is an unreliable and inconsistent development of blossoms and fruit, which can produce markedly reduced crop yields. Moreover, dormancy either does not occur, does not occur to an appreciable extent, or needs to be forced in regions that do not have an ideal natural climate for grape and other deciduous fruit growing. For example, tropical or semi-tropical areas, such as regions of Peru and Brazil, do not have any chilling. As another example, desert regions, such as the Coachella Valley in California or Hermosillo, Mexico, have insufficient chilling, and therefore dormancy does not occur to an appreciable extent. Even in regions with temperate or Mediterranean climates, there is the possibility of irregularity of dormancy.

These problems are of greater practical significance in those climates in which the necessary cold stimulus is absent. These problems can also occur with the use of cultivars that are not adapted to local conditions that lack dormancy.

There has been an effort to control bud dormancy by artificial intervention. Successful attempts have been made to interrupt bud dormancy by using natural and synthetic growth substances. U.S. Pat. No. 4,487,625 described methods of treatment the dormant buds of grapevines by use of an aqueous cyanamide solution with a content of 0.1-10 weight percent as a means for interrupting bud dormancy. Hydrogen cyanamide, for example Dormex®, Hi-Cane™, and other chemical equivalence of hydrogen cyanamide, have been used to break dormancy on fruit crops worldwide to compensate for a lack of winter chilling and/or to initiate an earlier and more even fruiting bud break. It is thought that Hydrogen cyanamide acts as a plant growth regulator. For example, Dormex® has been used to produce table grapes in regions with tropical or semi-tropical climates, such as the Sáo Francisco valley in Brazil, where the vines and plants do not attain sufficient chilling hours to initiate dormancy at all. In addition, Dormex® has been used to produce table grapes in desert climates such as California's Coachella Valley and Hermosillo in Mexico, where insufficient chilling occurs. As another example of the use of a version or chemical equivalent of hydrogen cyanamide, Hi-Cane™ has been used in the temperate climate of New Zealand on kiwifruit vines to initiate an earlier and more even fruiting bud break. However, hydrogen cyanamide is a skin and eye irritant, and is especially acute when used in combination with the consumption of alcohol. Moreover, grape and other fruits grown with the use of hydrogen cyanamide cannot be certified as organically grown. Also, over time, the use of hydrogen cyanamide can lower the fruitability of vines by as much as 20-30% per year. Finally, the drift of hydrogen cyanamide sprays can potentially injure nearby citrus trees.

Therefore, there remains a need in the art for a method of inducing bud break or dormancy break without the use of plant growth regulators or harsh chemicals such as hydrogen cyanamide. Insufficient dormancy of chilling creates nutritional inconsistency in the plants. These nutritional deficiencies or excesses are addressed by the formula of the present invention. Whereas Dormex®, Hi-Cane™, and any other version or equivalent of hydrogen cyanamide, overcome these inconsistencies by regulating the growth of the plants, the formulas of the present invention are not plant growth regulators and address the inconsistencies purely nutritionally. As a result, the compositions of the present invention work to produce a high enough percentage of fruiting buds to get commercially acceptable crop yields and/or to initiate an earlier and more even fruiting bud break in tropical or semi-tropical climates, in desert climates, and in temperate or Mediterranean climates. Moreover, the fruit obtained by the methods of this invention are not prevented from being certified organic.

SUMMARY OF THE INVENTION

In one embodiment, the invention provides methods for inducing or improving bud break of deciduous plants following dormancy, where the method includes the step of applying to such plants within a few days of dormancy-pruning one or more compositions by either foliar application, soil application, or both foliar application and soil application, wherein the one or more compositions together comprise at least either five, six, seven, eight, nine, or all of the components from the group consisting of nitrogen, phosphorus, potassium, calcium, magnesium, trace elements, acidifier, fulvic acid, humic acid, and seaweed; and also where hydrogen cyanamide or any version or chemical equivalent of hydrogen cyanamide is not applied to such plants within a few months of dormancy-pruning, such that the bud break of the plants are induced or improved. In addition, the methods can be used when the plants are grown in a tropical or semi-tropical climate, and where the dormancy is forced, by adding water to the soil at or about the time that the plants are pruned. In addition, these methods can be used in desert climates, or climates that are temperate or Mediterranean. The methods of the invention can regulate dormancy by the use of sprinkler irrigation for extended periods. Furthermore, the bud-breaker composition can also exclude components that would prevent the fruit produced from being certified organically grown. For example, the methods can be used when the plants are grapes, tree fruit, and/or kiwifruit.

In a second embodiment, the invention provides for a foliar application composition for inducing bud break of deciduous plants, which includes at least five, six, seven, or all of the components from the group consisting of nitrogen, phosphorus, potassium, calcium, magnesium, trace elements, fulvic acid, and seaweed. The compositions of the invention also do not contain hydrogen cyanamide or any version or chemical equivalent of hydrogen cyanamide. For example, the use of the composition of this invention would not prevent the fruit produced to be certified as organically grown.

In a third embodiment, the invention provides for a soil or drip application composition for inducing bud break of deciduous plants, which includes at least five, six, seven, eight, nine or all of the components from the group consisting of nitrogen, phosphorus, potassium, calcium, magnesium, trace elements, acidifier, fulvic acid, humic acid, and seaweed. The compositions of the invention also do not contain hydrogen cyanamide or any version or chemical equivalent of hydrogen cyanamide. For example, the use of the composition of this invention would not prevent the fruit produced to be certified as organically grown.

DETAILED DESCRIPTION OF THE INVENTION

As used herein, the singular forms "a," "an," and "the" include plural referents unless the context clearly dictates otherwise.

As used herein, "bud break" occurs after dormancy when the buds open revealing shoots, green leaves, and immature fruit. Bud break can occur naturally, such as with the warmth of early spring (typically March in the northern hemisphere, September in the southern hemisphere). Alternatively, bud break can occur by the application of specific chemicals, such as hydrogen cyanamide or the compositions of the present invention.

As used herein, the term "deciduous fruit" includes any fruit from a deciduous fruit trees, grape or kiwifruit vines, shrubs, or bushes. Examples of deciduous fruits include, but are not limited to, grapes, apples, pears, kiwifruit, cherries, apricots, peaches, plums, nectarines, pluots, apriums, and other stone fruits. Berries, such as blueberries and raspberries, are examples of fruits that can be grown from deciduous shrubs or bushes.

During frost in certain climates, deciduous plants enter a period referred to as "dormancy." In such a climate, the buds will leave dormancy after they have been exposed to enough degree days and then after the temperature begins to rise, such as in the Spring. However, in some climates, such as tropical or semi-tropical climates in order to produce acceptable crop yields, dormancy does not naturally occur. In such climates, the plants have to be forced into dormancy, for example, by withholding water. Also in some climates, such as desert climates, dormancy can be insufficient, or irregular. In such climates, sprinkler irrigation for extended periods, for example, has been employed to enhance normal dormancy.

As used herein, the term "tropical or semi-tropical climate" encompasses any climate in which dormancy does not occur naturally. Examples of tropical or semi-tropical climates include regions of Peru and Brazil, but these are not meant to be limiting examples. In tropical or semi-tropical climates, in order to achieve proper dormancy, plants must be forced into dormancy by, for example, depriving the plants of water for a sufficient period of time. In such a case, the plants can be moved out of dormancy by adding water to the soil. One possible way to add water is with the use of a dripper. The present invention includes methods for inducing "bud break" of plants in tropical or semi-tropical climates, as well as plants that are not in tropical or semi-tropical climates. For example, the methods of the present invention can be used in moderate desert climates, such as can be found in parts of the United States and Mexico. In such climates, the dormancy of the plants can be partially forced. The present invention can also be used in temperate or Mediterranean climates with adequate chilling hours and natural dormancy in order to initiate an earlier and more even fruiting bud break.

As used herein, the term "nitrogen" encompasses nitrogen from any source, including but not limited to sources that will not prevent crops grown with the source from being certified organically grown. For example, nitrogen can be obtained as water-soluble organic nitrogen and/or water insoluble organic nitrogen from BioLink 3-3-3 plus Micronutrient from Westbridge, Vista, Calif. 92081. Nitrogen can also be obtained as ammoniacal nitrogen and/or water soluble organic nitrogen from DynaMega 2-1-1 from Global Organics. However, the source of nitrogen, as considered by this invention, is not to be limited to the sources described herein, but it can be obtained from any other source that contains nitrogen.

As used herein, the term "phosphorus" encompasses phosphorus from any source, including but not limited to sources that will not prevent crops grown with the source from being certified organically grown. For example, phosphorus can be obtained from the available phosphoric acid ($P_2O_5$) from BioLink 3-3-3 plus Micronutrient from Westbridge, Vista, Calif. 92081. Phosphorus can also be obtained from the available phosphoric acid ($P_2O_5$) from DynaMega 2-1-1 from Global Organics, Goodyear, Ariz. 85338. However, the source of phosphorus, as considered by this invention, is not to be limited to the sources described herein, but it can be obtained from any other source that contains phosphorus.

As used herein, the term "potassium" encompasses potassium or potash from any source, including but not limited to sources that will not prevent crops grown with the source from being certified organically grown. For example, potassium can be obtained from the potash ($K_2O$) from BioLink 3-3-3 plus Micronutrient from Westbridge, Vista, Calif. 92081. Potassium can also be obtained from the potash of BioLink Micronutrient Fertilizer, also from Westbridge. Alternatively, potassium can be obtained from the potash of Organic Triggrr, also from Westbridge. Potassium can also be obtained from the potash ($K_2O$) from DynaMega 2-1-1 from Global Organics, Goodyear, Ariz. 85338. However, the source of potassium, as considered by this invention, is not to be limited to the sources described herein, but it can be obtained from any other source that contains potassium or potash.

As used herein, the term "calcium" encompasses calcium from any source, including but not limited to sources that will not prevent crops grown with the source from being certified organically grown. For example, calcium can be obtained from BioLink Cal Plus from Westbridge, Vista, Calif. 92081. However, the source of calcium, as considered by this invention, is not to be limited to the sources described herein, but it can be obtained from any other source that contains calcium.

As used herein, the term "magnesium" encompasses magnesium from any source, including but not limited to sources that will not prevent crops grown with the source from being certified organically grown. For example, magnesium can be obtained from the BioFlora Mg 4% from Global Organics, Goodyear, Ariz. 85338. Alternatively, magnesium can be obtained from the Fulmega 1% Mg. However, the source of magnesium, as considered by this invention, is not to be limited to the sources described herein, but it can be obtained from any other source that contains magnesium.

As used herein, the term "trace elements," "micronutrients," or "micro-trace elements" include one or more of the following, but need not include all, iron, manganese, zinc, copper, boron, cobalt, chloride, aluminum, bromide, fluoride, iodine, rhobidium, silicon, titanium, vanadium and molybdenum, or similar elements. Trace elements can be obtained from any source, including but not limited to sources that will not prevent crops grown with the source from being certified organically grown. For example, trace elements can be obtained from the trace elements found in BioLink Micronutrient Fertilizer from Westbridge, Vista, Calif. 92081, or any of the trace elements as indicated below. However, the source of trace elements, as considered by this invention, is not to be limited to the sources described herein, but it can be obtained from any other source that contains trace elements.

As used herein, the term "zinc" encompasses zinc from any source, including but not limited to sources that will not prevent crops grown with the source from being certified organically grown. For example, zinc can be obtained from the BioFlora Zn 7% from Global Organics, Goodyear, Ariz. 85338. However, the source of zinc, as considered by this invention, is not to be limited to the sources described herein, but it can be obtained from any other source that contains zinc.

As used herein, the term "iron" encompasses iron from any source, including but not limited to sources that will not prevent crops grown with the source from being certified organically grown. For example, iron can be obtained from the BioFlora Iron from Global Organics, Goodyear, Ariz. 85338. However, the source of iron, as considered by this invention, is not to be limited to the sources described herein, but it can be obtained from any other source that contains iron.

As used herein, the term "seaweed" encompasses seaweed from any source, including but not limited to sources that will not prevent crops grown with the source from being certified organically grown. For example, seaweed can be obtained from the seaweed from Global Organics Bioflora Seaweed Creme, Global Organics, Goodyear, Ariz. 85338. However, the source of seaweed, as considered by this invention, is not to be limited to the sources described herein, but it can be obtained from any other source that contains seaweed.

As used herein, the term "acidifier" encompasses citric acid, acetic acid, and any equivalent acid, from any source, including but not limited to sources that will not prevent crops grown with the source from being certified organically grown. For example, acidifier can be obtained by using any available citric acid, for example, citric acid approved for use on certified organically grown crops, or any available acetic acid, for example, acetic acid approved for use on certified organically grown crops. For example, the BioLink Acidifier from Westbridge, Vista, Calif. 92081 can be used. However, the source of the acidifier, as considered by this invention, is not to be limited to the sources described herein, but it can be obtained from any other source that contains citric acid, acetic acid, and any equivalent acid.

As used herein, the term "fulvic acid" encompasses fulvic acid from any source, including but not limited to sources that will not prevent crops grown with the source from being certified organically grown. For example, fulvic acid can be derived from leonardite or humus. Fulvic acid can be obtained from Fulvex and/or Fulmega 1% Mg, from Global Organics, Goodyear, Ariz. 85338. However, the source of fulvic acid, as considered by this invention, is not to be limited to the sources described herein, but it can be obtained from any other source that contains fulvic acid.

As used herein, the term "humic acid" encompasses humic acid from any source, including but not limited to sources that will not prevent crops grown with the source from being certified organically grown. For example, humic acid can be derived from leonardite or humus. Humic acid can be obtained from Humega, from Global Organics, Goodyear, Ariz. 85338. However, the source of humic acid, as considered by this invention, is not to be limited to the sources described herein, but it can be obtained from any other source that contains humic acid.

There is an increasing emphasis in developed countries on the production of food crops by use of certified organic crop production processes and materials. The governments of Canada, Australia, the United States, the European Union and other countries have developed standards for qualifying food products as "organic" or "organically produced," and several certifying organizations and government agencies exist to certify farms and market produce as "organic" under the appropriate standards. The concept underpinning "organic" food and crop production is that the inputs used in crop or animal production (fertilizer, seeds, feeds, sprays, etc.) are allowed to contain only minimal levels of certain approved non-natural materials, such as synthetic chemical fertilizers, genetically modified organisms, etc., and are allowed to contain essentially no amounts of designated undesirable materials, such as pesticides, drugs, growth hormones, pathogens, etc. The "certified organic" labeling and terminology have been developed to mean products or produce certified by recognized organizations as meeting the applicable agency standards and product or produce made by methods that meet the agency standards for organic production methods.

The bud breaker solutions, foliar application compositions, and/or drip (soil) application compositions of the present invention do not contain hydrogen cyanamide, or any version or chemical equivalent of hydrogen cyanamide. An example of a version or chemical equivalent of hydrogen cyanamide is calcium cyanamide. Dormex® is an example of commercially available hydrogen cyanamide. In addition, Hi-Cane™ is a water-based solution of hydrogen cyanamide that is used commonly in New Zealand for the production of kiwifruit. Therefore, the bud break solution, foliar application composition, and/or drip (soil) application composition of the present invention can replace Dormex®, Hi-Cane™, and any other version or equivalent of hydrogen cyanamide.

The bud breaker solutions, foliar application compositions and/or drip (soil) application compositions of the present invention are applied to the plants and/or soil to move the plants out of dormancy. For example, the solutions and/or compositions can be added to plants and the soil of plants in a tropical or semi-tropical climate at or around the same time that water is added to the soil after withholding it to force dormancy. At about the same time, or just before or just after water is added to the soil, the plants are pruned (referred to as "dormancy-pruning"). For example, the compositions of the present invention can be added within a few days of the dormancy pruning Advantageously, the compositions are added within 12 hours of dormancy pruning, but they can also be added within 24 hours, within 2 days, and even up to 5 days or more from dormancy pruning. In desert climates, the bud-breaker compositions can be added at the same time that Dormex® is normally added. Finally, in temperate or Mediterranean climates, the bud-breaker compositions can be added before bud break would naturally occur, to create an earlier bud break and a more even fruiting bud break. The compositions can be added to the plants with the use of a back-pack sprayer, a commercial sprayer (such as is pulled by a tractor), or by any other method that will cover the plants.

Ideally, the compositions of this invention are added within 12 hours of moving the plants out of dormancy, such as with dormancy pruning, but they can also be added within 24 hours, within 2 days, and even up to 5 days or more from dormancy pruning. The one or more compositions can be added by foliar application, by soil (drip) application, or by both. Moreover, when the compositions are added to both the plants (by foliar application) and soil (by drip application), it can be added by foliar application before soil application, it can be added by foliar application after soil application, or it can be added by foliar application at the same or approximately the same time as the soil application. Second, third, and additional applications of the compositions can be made after the initial application. For example, a second foliar application, drip application, or both can be added approximately 3 days, 5 days, 7-10 days, two weeks, or more than two weeks after the initial application or applications. This second application can, but need not necessarily, occur at first sign of bud break. As another example, a third foliar application, drip application, or both can be added approximately less than or at three weeks, four weeks, or more than four weeks after the initial application or applications. For example, this third application can, but need not necessarily, occur when the bud shoots are approximately 10 centimeters (4 inches) long. As such, the methods of this invention are not meant to be limited by the number of applications of the compositions of the invention.

The methods of the present invention induce bud break or dormancy break without the use of plant growth regulators or harsh chemicals, such hydrogen cyanamide. The nutritional deficiencies or excesses that can be caused in different regions, for example by insufficient dormancy or chilling, are addressed by the compositions of the present invention. Whereas Dormex®, Hi-Cane™, and any other version or equivalent of hydrogen cyanamide, overcome these inconsistencies by regulating the growth of the plants, the compositions of the present invention are not plant growth regulators and addresses the inconsistencies purely nutritionally. As a result, the compositions of the present invention work to produce a high enough percentage of fruiting buds to get commercially acceptable or viable crop yields in tropical or semi-tropical climates, in desert climates, and in temperate or Mediterranean climates.

It is therefore an advantage of this invention that bud break can be induced without the use of hydrogen cyanamide, such as Dormex® or Hi-Cane™. The use of Dormex® or Hi-Cane™ can decrease the fruitabitiy of plants over time. Therefore, one advantage of avoiding chemicals such as Dormex® or Hi-Cane™ is the preservation of the future fruitability of the plant. Moreover, the bud breaker compositions do not require any ingredients that would prevent the produced fruit from being marketed as certified organically grown. However, this is not meant that the compositions of the present invention are limited to components from organic sources, or that the compositions of the present invention cannot contain ingredients that would prevent the produced fruit from being certified organically grown. Another potential advantage of the present invention is that the application of the bud-breaker compositions could lead to an earlier and more uniform bud break, which could lead to a more uniform harvest in climates that have adequate chilling hours and natural dormancy, or with irregularity of the dormancy.

The compositions of the invention that can be applied to the plants by either foliar application, soil (drip) application, or both, comprise at least five of the components from the group consisting of nitrogen, phosphorus, potassium, calcium, magnesium, trace elements, acidifier, fulvic acid, humic acid, and seaweed. It is anticipated that the at least five components are added to the plants, regardless of whether they are added by foliar application, soil (drip) application, or both. In fact, for example, a subset of components can be added by foliar application and the same or a different subset of components can be added by soil (drip) application, provided that at least five or more of the components are added to the plant. Moreover, one or more than one compositions can be applied by foliar application, and one or more than one compositions can be applied by soil (drip) applications, and one or more than one compositions can be applied by both foliar and soil (drip) application.

It is possible, but not required, that all of the components will be included in the one or more compositions of the invention. However, it is also possible that not all of the components will be required to induce or improve bud break. This is due, in part, to the variability of the soil in various regions, as well as the variability of the soil in a particular region. Therefore, depending on the quality and composition of the soil, all or less than all of the components may be required. For example, if the soil is particularly rich in magnesium, the compositions of this invention may or may not need to include the magnesium component. Thus, the compositions of this invention may include five, six, seven, eight, nine, or all of the components.

EXAMPLE 1

Grapevines of table grape varietals growing in the tropical climate of Peru or Brazil are forced into dormancy by the depletion of water and pruning Approximately 20-30 days before the desired bud break, these grapevines are pruned and water is added. In addition, the plant-applied fertilizer bud-breaker composition foliar formula is added to the grapevines just after pruning, within a day after pruning by spraying to get full coverage of the plant in order to achieve bud break.

| Plant-Applied Fertilizer Bud-Break composition Formula (In 100 gallon $H_2O$) | | |
|---|---|---|
| 1. | BioLink 3-3-3 plus Micronutrient | 2 quarts per 100 gallon |
| 2. | BioLink Cal Plus | 2 quarts per 100 gallon |
| 3. | BioLink Micronutrient Fertizer | 2 quarts per 100 gallon |
| 4. | Triggrr | 1 quarts per 100 gallon |
| 5. | BioLink Acidifier | 1 quarts per 100 gallon |
| 6. | DynaMega 2-1-1 | 2 quarts per 100 gallon |
| 7. | Fulvex | 2 quarts per 100 gallon |
| 8. | BioFlora Seaweed Creme | 2 quarts per 100 gallon |
| 9. | Citric Acid | Quantity depends on acidity of the water |

Depending on the particular plants, approximately 100-200 gallons of Plant-Applied fertilizer Bud-Break composition per acre is sprayed on the vines. In addition, just after pruning, approximately on the day after pruning, separately 10 gallons per acre of Humega, 2.5 gallons per acre of Fulvex, 0.5 quarts per acre of BioLink Acidifier, and 2 quarts per acre of BioFlora Seaweed Creme (the combination of which is the soil-applied fertilizer bud-breaker composition) is run through a dripper or through the irrigation system. The dry soil is totally saturated. Approximately three days later, both the plant-applied fertilizer bud-breaker composition formula is sprayed on the plants again, and the soil-applied fertilizer bud-breaker composition formula both (at the same concentrations using the same composition) is added again at this time. Finally, at bud swell, both the plant-applied fertilizer bud-break composition formula is sprayed on the vines, and the soil-applied bud-break composition formula is applied through the irrigation system (both at the same concentrations using the same formulas).

EXAMPLE 2

Organic Crimson Seedless and Organic Superior Seedless grapes were grown in Peru according to the compositions in Example 1, with only slight variation in the application of the composition. However, these variations did not differ significantly from those found in Example 1. In addition, These trials were conducted on conventional grapes with poor fertility. Organic bud breaker compositions were applied to half of the rows and/or vines, while the conventional bud breaker, Dormex, was applied to the other half as a control group. The first application of both the organic and conventional bud breaker was the first week of August. The trials were inspected in December. The Organic Superior yield was 5 tons/hectare, and the conventional Superior yield was 6 tons/hectare. The Organic Crimson yield was 2 tons/hectare, and the conventional Crimson yield was 3 tons/hectare. However, the color of the organic Crimson was very good, and noticeably better than that of the conventional Crimsons. In addition, 8 mm of rain in October caused damage to the Superiors in the trial because they were already close to maturity. As a result, 100% of the conventional Superior bunches had berries split on the ends with cracking and mold due to rain damage. However, surprisingly, only 60% of the organic Superior bunches had berries that were split on the ends with cracking and mold due to rain damage.

EXAMPLE 3

Organic Sugraone and Crimson Seedless grapes growing in the tropical climate of Peru are forced into dormancy by the depletion of water and pruning. Before the desired bud break, these grapevines are pruned as normal, and water is added to the soil (as long as is normally required to break dormancy, but at least for a minimum of 8 hours). At the time that water is added to the soil, the "First Foliar Application" is applied. The First Foliar Application is added immediately after pruning, but no later than 12-24 hours after pruning. The materials for the First Foliar Application are added to the barrel in the order listed and premixed thoroughly before being put into the spray tank. 1000 liters of water is used per hectare for full coverage of all wood surfaces excluding the trunk. Pressure is around 200 pounds per square inch.

| | First Foliar Application Formula (In 1000 liters $H_2O$) | |
|---|---|---|
| 1. | BioFlora DynaMega | 2.2 liters per hectare |
| 2. | BioFlora Zn 7% | 0.65 liters per hectare |
| 3. | BioFlora Mg 4% | 0.65 liters per hectare |
| 4. | BioFlora Iron | 0.65 liters per hectare |
| 5. | BioFlora Fulmega 1% Mg | 1.18 liters per hectare |

The "First Drip Application" is applied after the post-pruning water application and after the first foliar application, but no later than one day after pruning. The materials for the First Drip Application are added to a barrel and premixed thoroughly with water before being applied thru the dripper. The mix is slowly applied into the drip lines over a 2-3 hour period. After, at least 3-4 hours of fresh water should be applied to clear the lines and get the material into the root zone.

| | First Drip Application Formula | |
|---|---|---|
| 1. | Humega | 86.75 liters per hectare |
| 2. | BioFlora Seaweed Creme | 5.92 liters per hectare |
| 3. | Cal Plus | 3.96 liters per hectare |
| 4. | BioFlora Fulmega 1% Mg | 1.18 liters per hectare |
| 5. | BioFlora Zn 7% | 2.83 liters per hectare |
| 6. | BioFlora Mg 4% | 2.83 liters per hectare |
| 7. | BioFlora Iron | 1.26 liters per hectare |

The "Dynamega Application" is applied by drip one day after the first drip application: Dynamega—4.73 liters per hectare. The "First Acidifier Application" is applied by drip two days after the first drip application (and one day after the Dynamega application): Acidifier—0.475 liters per hectare.

The "Second Drip Application" is applied at the first sign of bud-break, approximately 7-10 days after the first drip application. Water is applied to the grapevines for a minimum of 2-3 hours before the second drip application. The materials for the second drip application are added to a barrel in the order below and premixed thoroughly with water before being applied thru the dripper. The mix is slowly applied into the drip lines over a 2-3 hour period. After, at least 3-4 hours of fresh water should be applied to clear the lines and get the material into the root zone.

| | Second Drip Application Formula | |
|---|---|---|
| 1. | Humega | 86.75 liters per hectare |
| 2. | BioFlora Seaweed Creme | 5.92 liters per hectare |
| 3. | Cal Plus | 3.96 liters per hectare |

As soon as possible after the second drip application is started, the "Second Foliar Application" is applied. The materials for the Second Foliar Application are added to the barrel in the order listed and premixed thoroughly before being put into the spray tank. 1000 liters of water is used per hectare for full coverage of all wood surfaces excluding the trunk. Pressure is around 200 pounds per square inch.

| | Second Foliar Application Formula (In 1000 liters $H_2O$) | |
|---|---|---|
| 1. | BioFlora DynaMega | 2.2 liters per hectare |
| 2. | BioFlora Zn 7% | 0.65 liters per hectare |
| 3. | BioFlora Mg 4% | 0.65 liters per hectare |
| 4. | BioFlora Iron | 0.65 liters per hectare |
| 5. | BioFlora Fulmega 1% Mg | 1.18 liters per hectare |

The "Second Acidifier Application" is applied by drip one day after the second drip application: Acidifier—0.316 liters per hectare.

The "Third Drip Application" is applied when the bud shoots are approximately 10 centimeters (4 inches) long. Water is applied to the grapevines for a minimum of 2-3 hours before the third drip application. The materials for the third drip application are added to a barrel in the order below and premixed thoroughly with water before being applied thru the dripper. The mix is slowly applied into the drip lines over a 2-3 hour period. After, at least 3-4 hours of fresh water should be applied to clear the lines and get the material into the root zone.

| Third Drip Application Formula | | |
| --- | --- | --- |
| 1. | Humega | 86.75 liters per hectare |
| 2. | Cal Plus | 3.96 liters per hectare |

As soon as possible after the third drip application is started, the "Third Foliar Application" is applied. The materials for the third foliar application are added to the barrel in the order listed and premixed thoroughly before being put into the spray tank. 1000 liters of water is used per hectare for full coverage of all leaf and wood surfaces, excluding the trunk. Pressure is around 200 pounds per square inch.

| Third Foliar Application Formula (In 1000 liters $H_2O$) | | |
| --- | --- | --- |
| 1. | BioFlora DynaMega | 2.2 liters per hectare |
| 2. | BioFlora Zn 7% | 0.65 liters per hectare |
| 3. | BioFlora Mg 4% | 0.65 liters per hectare |
| 4. | BioFlora Iron | 0.65 liters per hectare |
| 5. | BioFlora Fulmega 1% Mg | 1.18 liters per hectare |

The "Second Fulmega Drip Application" is applied as soon as possible after the third drip application: Fulmega 1% Mg—14.12 liters per hectare.

7-14 days after bloom ("post bloom"), the "Fourth Foliar Application" is applied. The materials for the fourth foliar application are added to the barrel in the order listed and premixed thoroughly before being put into the spray tank. 1000 liters of water is used per hectare for full coverage of all leaf and wood surfaces, excluding the trunk. Pressure is around 200 pounds per square inch.

| Fourth Foliar Application Formula (In 1000 liters $H_2O$) | | |
| --- | --- | --- |
| 1. | BioFlora DynaMega | 2.2 liters per hectare |
| 2. | Sea Cream | 1.9 liters per hectare |
| 3. | Cal Plus | 1.9 liters per hectare |
| 4. | BioFlora Fulmega 1% Mg | 1.6 liters per hectare |

At Verasion ("berry softening"), the "Fifth Foliar Application" is applied. The materials for the fifth foliar application are added to the barrel in the order listed and premixed thoroughly before being put into the spray tank. 1000 liters of water is used per hectare for full coverage of all leaf and wood surfaces, excluding the trunk. Pressure is around 200 pounds per square inch.

| Fifth Foliar Application Formula (In 1000 liters $H_2O$) | | |
| --- | --- | --- |
| 1. | BioFlora DynaMega | 2.2 liters per hectare |
| 2. | Sea Cream | 1.9 liters per hectare |
| 3. | Cal Plus | 1.9 liters per hectare |
| 4. | BioFlora Fulmega 1% Mg | 1.6 liters per hectare |

The initial foliar and drip (soil) applications are important for inducing or improving bud break. However, some of the applications are required for good general agronomic practice, and therefore not all of the application described above are necessarily required for the present invention. Those skilled in the art will understand how to apply good general agronomic procedures for the plants in their particular region. For example, additional components can be added to the soil or to the plants as needed in a particular region or soil type for good general agronomic practice.

All patents, patent applications, and other scientific or technical writings referred to anywhere herein are incorporated by reference in their entirety. The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by embodiments, optional features, modification and variation of the concepts herein disclosed may be resorted to by those skilled in the art, and that such modifications and variations are considered to be within the scope of this invention as defined by the description and the appended claims.

What is claimed is:

1. A method for inducing or improving bud break of deciduous plants to produce a crop of fruit following dormancy, comprising the step of applying to such plants within five days of dormancy-pruning one or more compositions by either foliar application, soil application, or both foliar application and soil application, wherein the one or more compositions together comprise at least seven of the components from the group consisting of nitrogen, phosphorus, potassium, calcium, magnesium, a trace element, acidifier, fulvic acid, humic acid, and seaweed; and further wherein hydrogen cyanamide or any chemical version or equivalent of hydrogen cyanamide is not applied to such plants within a few months of dormancy-pruning, such that the bud break of the plants are induced or improved to produce a crop of fruit.

2. The method of claim 1, wherein the one or more compositions together comprise at least eight of the components from the group consisting of nitrogen, phosphorus, potassium, calcium, magnesium, a trace element, acidifier, fulvic acid, humic acid, and seaweed.

3. The method of claim 1, wherein the one or more compositions together comprise at least nine of the components from the group consisting of nitrogen, phosphorus, potassium, calcium, magnesium, a trace element, acidifier, fulvic acid, humic acid, and seaweed.

4. The method of claim 1, wherein the one or more compositions together comprise all of the components from the group consisting of nitrogen, phosphorus, potassium, calcium, magnesium, a trace element, acidifier, fulvic acid, humic acid, and seaweed.

5. The method of claim 1, wherein the plants are grown in a tropical or semi-tropical climate, and wherein the dormancy was forced, further comprising the step of adding an effective amount of water to the soil at or about the time that the plants are pruned, in order to move the plants out of dormancy.

6. The method of claim 5, wherein the deciduous plants are grapes.

7. The method of claim 6, wherein no component is applied to the plants that would prevent the fruit produced from being organically certified.

8. The method of claim 1, wherein the plants are grown in a desert climate.

9. The method of claim 8, wherein the deciduous plants are grapes.

10. The method of claim 8, wherein the deciduous plants are tree fruit.

11. The method of claim 8, wherein the deciduous plants are kiwifruit.

12. The method of claim 8, wherein the dormancy is regulated by the use of sprinkler irrigation for extended periods.

13. The method of claim 1, wherein the plants are grown in temperate or Mediterranean climates.

14. The method of claim 13, wherein the deciduous plants are kiwifruit.

15. The method of claim 13, wherein the deciduous plants are grapes.

16. The method of claim 13, wherein the deciduous plants are tree fruit.

17. A method for inducing or improving bud break of deciduous plants to produce a crop of fruit that have had no chilling or insufficient chilling for adequate dormancy, comprising the step of applying to such plants within five days of pruning one or more compositions by either foliar application, soil application, or both foliar application and soil application, wherein the one or more compositions together comprise at least seven of the components from the group consisting of nitrogen, phosphorus, potassium, calcium, magnesium, a trace element, acidifier, fulvic acid, humic acid, and seaweed; and further wherein hydrogen cyanamide or a chemical equivalent of hydrogen cyanamide is not applied to such plants within four months of pruning, such that the bud break of the plants are induced or improved to produce a crop of fruit.

18. The method of claim 17, wherein the deciduous plants are grapes.

19. The method of claim 17, wherein the deciduous plants are tree fruit.

20. The method of claim 17, wherein the deciduous plants are kiwifruit.

21. The method of claim 17, wherein the plants are grown in a tropical or semi-tropical climate, and wherein the dormancy was forced, further comprising the step of adding an effective amount of water to the soil at or about the time that the plants are pruned, in order to move the plants out of dormancy.

22. The method of claim 17, wherein the plants are grown in a desert climate.

23. The method of claim 22, wherein the dormancy is regulated by the use of sprinkler irrigation for extended periods.

24. The method of claim 17, wherein the plants are grown in temperate or Mediterranean climates.

25. A method for inducing or improving bud break of deciduous plants to produce a crop of fruit that have had no chilling or insufficient chilling for adequate dormancy, comprising the step of applying to such plants within five days of pruning one or more compositions by either foliar application, soil application, or both foliar application and soil application, wherein the one or more compositions together comprise at least seven of the components from the group consisting of nitrogen, phosphorus, potassium, calcium, magnesium, a trace element, acidifier, fulvic acid, humic acid, and seaweed; and further wherein hydrogen cyanamide or a chemical equivalent of hydrogen cyanamide is not applied to such plants at the same time, such that the bud break of the plants are induced or improved to produce a crop of fruit.

26. The method of claim 25, wherein the deciduous plants are grapes.

27. The method of claim 25, wherein the deciduous plants are tree fruit.

28. The method of claim 25, wherein the deciduous plants are kiwifruit.

* * * * *